United States Patent [19]
Shihata

[11] Patent Number: 5,207,232
[45] Date of Patent: May 4, 1993

[54] DEVICE AND METHOD FOR INTRAVAGINAL, BARRIER-TYPE PREVENTION OF CONCEPTION AND INFECTION

[75] Inventor: Alfred A. Shihata, 13565 Mira Montana Dr., Del Mar, Calif. 92014

[73] Assignee: Alfred A. Shihata, San Diego, Calif.

[21] Appl. No.: 716,644

[22] Filed: Jun. 17, 1991

Related U.S. Application Data

[63] Continuation-in-part of Ser. No. 593,687, Oct. 5, 1990, abandoned, which is a continuation of Ser. No. 386,882, Jul. 31, 1989, Pat. No. 4,989,618, which is a continuation of Ser. No. 159,846, Feb. 24, 1988, Pat. No. 4,858,624.

[51] Int. Cl.$^5$ .............................................. A61F 6/06
[52] U.S. Cl. ..................................... 128/837; 128/838
[58] Field of Search ............... 128/830, 834, 835, 837, 128/838, 841, 833

[56] References Cited

U.S. PATENT DOCUMENTS

| | | | |
|---|---|---|---|
| 1,634,555 | 7/1927 | Peloubet | 128/834 X |
| 2,071,248 | 2/1937 | Campbell | 128/837 |
| 2,104,275 | 1/1938 | Schleicher | 128/838 |
| 2,110,962 | 3/1938 | Munro | 128/832 X |
| 2,157,689 | 5/1939 | Clark, Jr. | 128/837 |
| 2,218,009 | 10/1940 | Schmitz, Jr. | 128/838 |
| 2,324,656 | 7/1943 | Vincent | 128/837 |
| 2,551,618 | 5/1951 | Mayer | 128/841 |
| 3,128,762 | 4/1964 | Young | 128/834 |
| 3,130,721 | 4/1964 | Young | 128/837 |
| 4,031,886 | 6/1977 | Morhenn | 128/837 |
| 4,286,593 | 9/1981 | Place et al. | 128/832 |
| 4,381,771 | 5/1983 | Gabbay | 128/129 |
| 4,848,363 | 7/1989 | Cattanach | 128/834 |

FOREIGN PATENT DOCUMENTS

| | | |
|---|---|---|
| 517159 | 10/1955 | Canada ........................ 128/838 |
| 845832 | 8/1949 | Fed. Rep. of Germany . |
| 363976 | 8/1906 | France . |
| 473023 | 12/1914 | France . |

*Primary Examiner*—Robert A. Hafer
*Assistant Examiner*—Brian E. Hanlon
*Attorney, Agent, or Firm*—Baker, Maxham, Jester & Meador

[57] ABSTRACT

A kit for intravaginal, barrier-type prevention of conception and sexually-transmitted infection includes a barrier-type device and an applicator, the barrier-type device including a cervical dome having an upwardly facing opening and a curved surface extending from the opening to a downwardly-facing dome peak and including a continuous fornical rim defining the opening and transitioning therefrom into a continuous, annular vaginal brim which circumscribes the dome and extends both outwardly and downwardly, and wherein the brim defines a thickened grip portion extending inwardly toward the dome. The applicator includes an elongate handle having at its proximal end arcuate support means for supporting the barrier-type device, and gripping member for releasably holding the device upon the support means during intravaginal positionment of said device.

30 Claims, 5 Drawing Sheets

DEVICE AND METHOD FOR INTRAVAGINAL, BARRIER-TYPE PREVENTION OF CONCEPTION AND INFECTION

REFERENCE TO RELATED APPLICATIONS

This application is a continuation-in-part of co-pending application Ser. No. 07/593,687, filed Oct. 5, 1990 abandoned Aug. 7, 1991, which is a continuation of application Ser. No. 07/386,882, filed Jul. 31, 1989, U.S. Pat. No. 4,989,618, which is a continuation of application Ser. No. 07/159,846 U.S. Pat. No. 4,858,624, filed Feb. 24, 1988.

FIELD OF THE INVENTION

The present invention relates to the field of contraceptive devices, and in particular, to a barrier-type device for the prevention of conception and infection by sexually-transmitted diseases.

BACKGROUND OF THE INVENTION

The prior art devices for intravaginal, barrier-type prevention of conception and sexually transmitted disease include the diaphragm and the cervical cap. The diaphragm, when seated intravaginally, acts as a barrier to prevent sperm from entering the os of the cervix. A spermicide is used on the inside of the diaphragm to kill sperm traversing over the edge of the diaphragm. Characteristically, the diaphragm is a shallow rubber cup with a rim. A round, coiled metal spring is disposed in the rim. The diaphragm is intended for intravaginal disposition between the posterior aspect of the pubic bone and the posterior fornix. When thus seated, the diaphragm presses against the vaginal wall to form a continuous barrier therewith.

The cervical cap is a small, vaulted or domed device, more rigid than the diaphragm, and dimensioned to fit over a cervix, where it is retained by suction, rather than spring tension, as is the diaphragm. The cap includes a dome which rises from a rim. The cap is slipped over the cervical protrusion to block access to the uterus through the cervical os.

None of these barrier-type devices is adapted to fit in close anatomical sealing engagement between the vagina and the cervix. The diaphragm is held against the upper part of the vaginal canal by the tension of the spring in its rim, while the cervical cap typically engages only the tip of the cervix. Both of these devices can be dislodged by sexual arousal, coital activity, or orgasm. As is known, such dislodgement can reduce the effectiveness of the barrier and permit unintended fertilization or unwanted infection, or worse, both.

In failing to take into account the anatomy and physiology of the vagina and the cervix, the prior art barrier-type devices form imperfect barriers against the penetration of sperm and agents of sexually transmitted diseases into the uterus. As is known, fertilization and infection take place within the uterus, therefore, the more sound the barrier to the cervical os, the greater the likelihood of preventing such fertilization or infection. With the emergence of the AIDS (acquired immune deficiency syndrome) epidemic, the risk of life-threatening infection accompanying heterosexual activity is increasing steadily. Therefore, there is a compelling need for intravaginal, barrier-type devices which can substantially decrease the risk of infection by significantly increasing the effectiveness and reliability of the barrier to entry of bodily fluids such as semen, into the cervix.

Another problem with many of the prior art devices, and with diaphragms and cervical caps in general, is the difficulty associated with proper positionment and engagement of the device with the cervix and vaginal walls to ensure the best possible seal. One feature of the device disclosed herein and in related U.S. Pat. No. 4,858,624 is a vaginal brim which has an increasing height from an anterior vaginal location to a posterior vaginal location. In order to significantly enhance the sealing characteristics, the device is to be positioned with the anterior portion of the brim engaged with the anterior vaginal wall and the posterior portion of the brim engaged with the posterior vaginal wall. What is needed then are means to help insert the device and insure its proper orientation with respect to the vaginal walls.

SUMMARY OF THE INVENTION

Generally speaking, there is provided a kit for the intravaginal, barrier-type prevention of conception and sexually-transmitted infection.

The kit includes a barrier-type device and an applicator. The barrier-type device includes a cervical dome having an upwardly facing opening and a curved surface extending from the opening to a downwardly facing dome peak and includes a continuous fornical rim defining the opening and transitioning from the dome into a continuous, annular vaginal brim which circumscribes the dome and extends both outwardly and downwardly, and wherein the brim defines a thickened grip portion extending inwardly toward the dome. The applicator includes an elongate handle having at its proximal end an arcuate support member for supporting the barrier-type device, and gripping means for releasably holding the device upon the support member during intravaginal positionment of said device. The gripping means includes a plunger slidably disposed in the handle and having a proximal tip extendable forwardly of the proximal end, and the applicator being adapted to grip the thickened grip portion of the brim of the device between the proximal tip and the proximal end of the handle and pull and hold the grip portion into a channel defined in the proximal end of the handle.

A portion of the invention is based upon the inventor's critical observation that a barrier-type device engaging the cervix and the vagina by seating at the bottom of the fornices and then folding back from the fornices along the interior vaginal walls provides a barrier adapted to the anatomy and physiology of the vagina in the vicinity of the cervix which not only forms a reliable, effective seal, but also resists displacement during arousal, intercourse, and orgasm.

The device conforms to and sealingly engages the vagina in the vicinity of the cervix. The sealing engagement of the device with the vagina is continuous during all of the expected physiological changes which the vagina and cervix undergo as the result of, for example, sexual activity and menstrual cycle.

It is an object of the present invention to provide an improved device for providing intravaginal, barrier-type prevention of conception and sexually-transmitted infection.

It is another object of the present invention to provide an intravaginal, barrier-type device which accounts for, and takes advantage of, the anatomy and physiology of the vagina in the vicinity of the cervix to form a more perfect and a more reliable seal against the movement of sperm and micro-organisms from the vaginal canal through the cervical os into the uterus.

It is still another object of the present invention to provide a barrier-type device for the prevention of conception and sexually-transmitted infection which is easy to insert and remove.

Further objects and advantages of the present invention will become apparent from the following description of the preferred embodiment.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
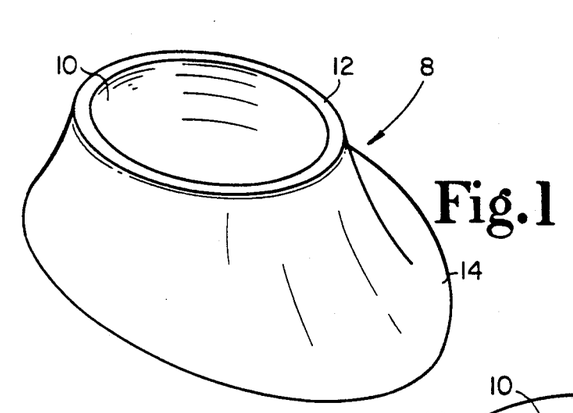
FIG. 1 illustrates a perspective view of the barrier-type device of the invention.
Figure 2:
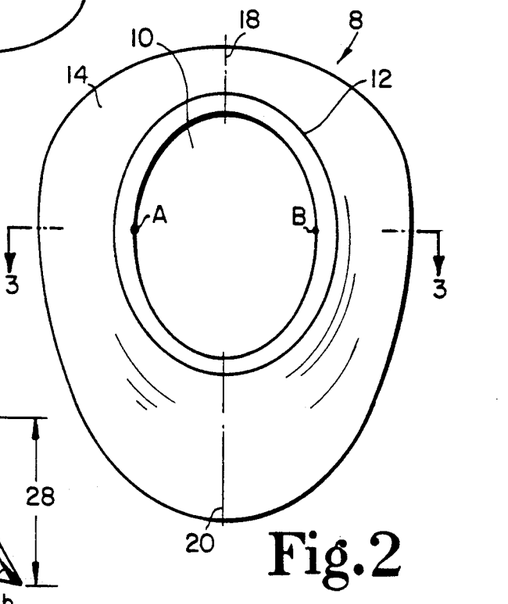
FIG. 2 is a plan view of the device.
Figure 3:
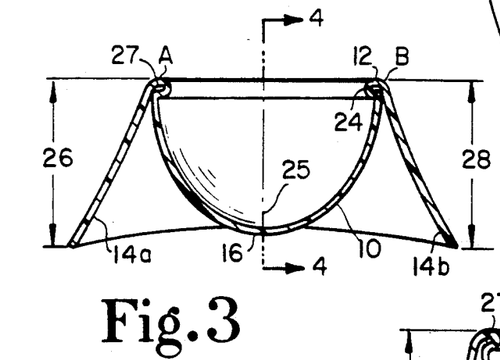
FIG. 3 is a sectional view of the device taken along lines 3—3 of FIG. 2.
Figure 4:
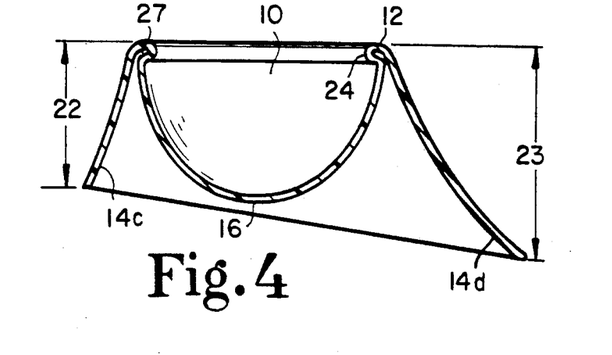
FIG. 4 is a sectional view, rotated 90° from FIG. 3, and taken along lines 4—4 of FIG. 3.

An intravaginal, barrier-type device for preventing conception and infection by sexually-transmitted diseases is illustrated structurally in FIGS. 1-4. Preferably, the device is a single piece formed by molding a flexible, physiologically non-reactive material, such as silicone rubber. The device 8 includes a cervical dome 10. The dome preferably has a hemi-spherical or hemi-ovoid shape which forms a cervical enclosure. At the opening of the enclosure, the dome 10 transitions to a fornical rim 12 which, in turn, transitions by a backward fold to a vaginal brim 14. As best seen in FIGS. 3 and 4, the dome has a peak, or top, 16.

As FIGS. 1-4 reveal, the vaginal brim circumscribes, or surrounds, the dome and extends downwardly from the rim 12. The brim exhibits lateral symmetry, as illustrated in FIG. 3, where the lateral extensions 14a and 14b of the brim 14 are substantially equal in form and dimension. The width of the brim increases continuously from the anterior to the posterior of the device 8. This increase is revealed in FIGS. 1 and 4. In FIG. 4, the anterior extension 14c of the brim 14 has a smaller dimension 22 than the dimension 23 at the posterior extension 14d of the brim 14. The brim also has an outward bias, or curve, to it, as seen in FIGS. 1, 3, and 4.

The width of the brim increases with circumferential symmetry from an anterior vaginal location 18 on the anterior extension 14c of the brim to a posterior vaginal location 20 on the posterior portion 14d of the brim. The circumferential symmetry of the brim 14 is illustrated in FIG. 2. In FIG. 2, point A over the lateral extension 14a is displaced in a counterclockwise direction on the rim 12 from the anterior vaginal location by a rim segment equal to the rim segment by which the point B over the lateral extension 14B is displaced on the rim 12 clockwise from the anterior vaginal location 18. As shown in FIG. 3, the dimension 26 reflecting the width of the brim at extension 14a is equal to the dimension 28 reflecting the width of the brim at extension 14b.

An annular lip 24 is formed in the device 8 by an inward extension of the rim 12 along the periphery of the opening into the dome 10. The lip 24 juts into the opening toward the center line 25 of the dome 10. The backward fold of the rim 12 at the lip 24 by which the rim 12 transitions to the brim 14 forms an annular groove 27 between the brim 14 and dome 10.

Figure 5:
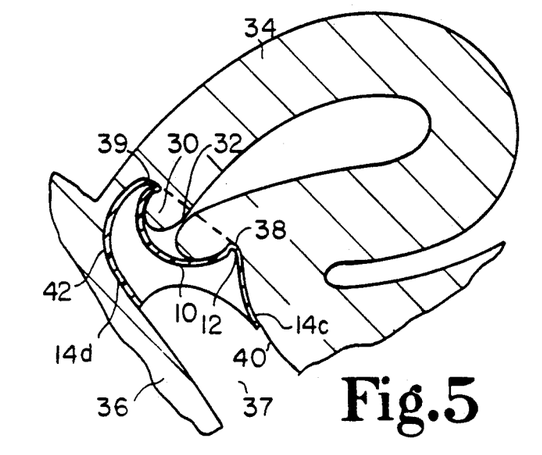
FIG. 5 is a partial, sagittal section of female sexual anatomy showing, in schematic representation, the posterior aspect of the vaginal tract and the barrier-type device in place covering the cervix, and sealing to the posterior of the vaginal canal.
Figure 6:
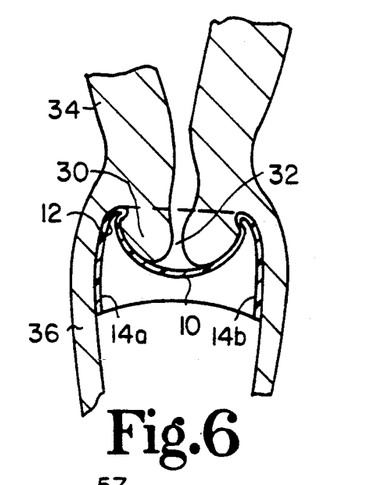
FIG. 6 illustrates a schematic of the posterior of the vaginal canal from a frontal aspect showing the barrier-type device in place.

The significance of the structure of the barrier-type device 8 is illustrated in FIGS. 5 and 6. In FIGS. 5 and 6, female anatomy is conventionally illustrated as including a cervix 30 through which the cervical os 32 opens to the interior of the uterus 34. The vagina 36 includes an inner surface 37 which transitions to the cervix 30 by way of a fornix, an anatomical fold or recess. As is known, the fornix increases in depth from its anterior to its posterior aspects, which are usually referred to as the anterior fornix 38 and the posterior fornix 39, respectively. Further, at its rear, the vagina 36 transitions, by way of the anterior vaginal wall 40 to the anterior fornix 38, and by way of the posterior vaginal wall 42 to the posterior fornix 39. As shown in the frontal cross-section of FIG. 6, the fornices are laterally symmetrical.

FIGS. 5 and 6 illustrate how the barrier-type device of FIGS. 1-4 is adapted to the anatomy and physiology of the vagina in the vicinity of the cervix. As shown in FIGS. 3, 4, and 5, the proper orientation of the device 8 finds the cervical dome 10 engaging the cervix, which extends through the opening defined by the rim 12. The rim is seated at the bottom of the fornices. The annular lip 24 grips the bottom of the cervix at the fornices, thereby forming a circumferential seal. The brim 14 extends from the bottom of the fornices in close sealing engagement with the walls of the vagina, thereby continuing the circumferential seal along the vagina forwardly from the fornices. The barrier-type device is oriented with respect to the cervix to place the anterior extension 14c against the anterior vaginal wall 40, in the vicinity of the anterior fornix. Similarly, the posterior extension 14d is oriented to engage the posterior vaginal wall 42 in the vicinity of the posterior fornix. As shown in FIG. 6, the orientation of FIG. 5 disposes the lateral brim extensions 14a and 14b against the lateral vaginal walls in the vicinity of the lateral fornices.

As shown in FIGS. 5 and 6, not only does the device seal to the vagina and cervix, it orients the annular groove 27 toward the opening of the vagina. Thus oriented, the groove 27 will trap fluids traveling along the inside of the brim 14 toward the dome 10 and act as a reservoir for the spermicide.

In use, a spermicide such as NONOXYNOL-9 is applied to the total surface of the device 8, and the device is inserted into the vagina to engage the cervix with the orientation illustrated in FIGS. 5 and 6. Thus seated, the barrier-type device of the invention will seal from the base of the cervix, in the fornices and continuously and circumferentially along the vagina. This seal is superior to the prior art barrier devices. As is known, the diaphragm would engage only the posterior fornix, extending across the top of the vaginal wall forward to the posterior aspect of pubic bone. The cervical cap engages only the top of the cervix, and, generally, does not extend fully into the fornices. However, the device 8 fits precisely to the anatomy and physiology of the vagina in the vicinity of the cervix. Such an anatomically adapted form will not only seal effectively when the device is seated, but will also seal reliably by resisting unintentional displacement or dislodgement. The device is retained in place by suction exerted in the cervix by the dome 10, by the grip exerted on the base of the cervix by the annular lip 24, by a snug fitting between the rim 12 and the fornices, and by the outward curve of the brim, which flattens against the vagina. All of these mechanisms help prevent dislodgement of the device and contribute to the seal which the device makes.

Figures 7, 8, 9, 10:
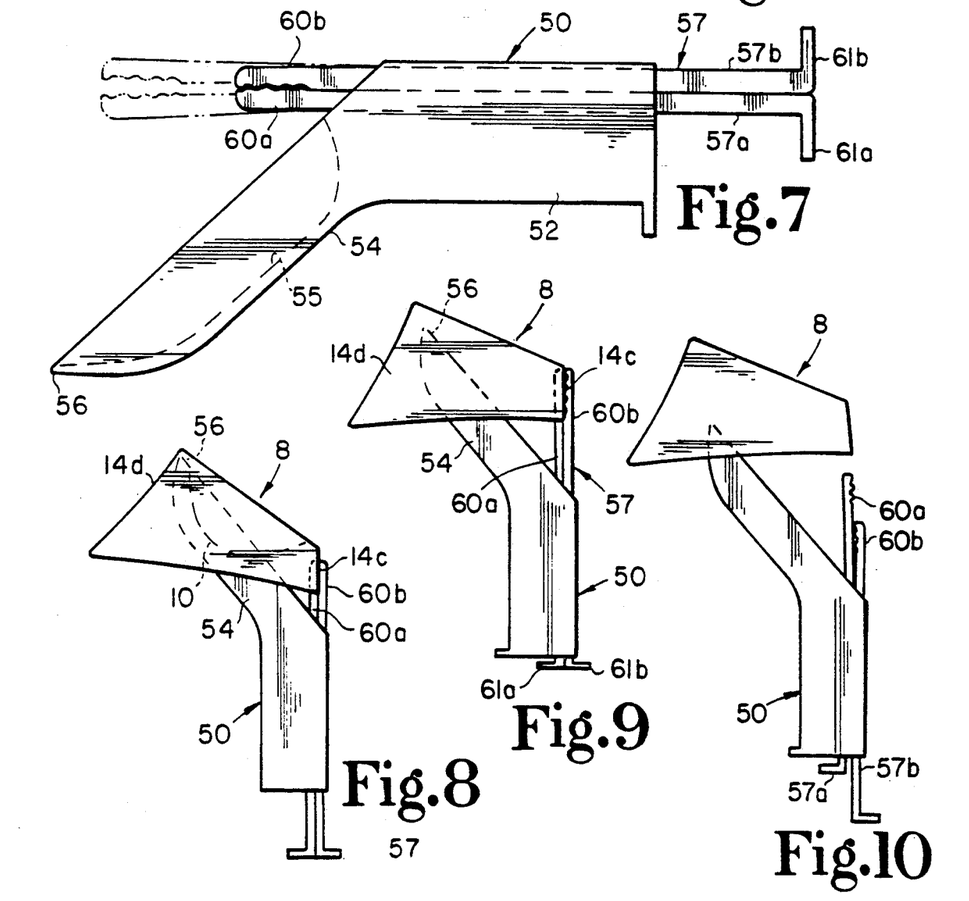
FIGS. 7-10 illustrate the structure and operation of the applicator for insertion of the barrier-type device of FIGS. 1-6 into the vagina.

An applicator for intravaginal placement of the barrier-type device 8 is illustrated in FIGS. 7–10. The applicator 50 consists of a speculum-type portion with a main body, or a handle, 52 which transitions into projection 54 having an angle of, preferably, 40° with the main body 52. As seen in FIG. 7, the angled projection 54 has a concave recess 55. A rounded forward edge 56 is provided on the proximal end of the projection 54. A movable inserter 57 is slidably disposed in the main portion 52 and moved in the main portion between a first position, indicated by the solid lines in FIG. 7, and a second, release, position denoted in FIG. 7 by the interrupted lines. The inserter 57 consists of two equivalent elongate pieces 57a and 57b having serrated forward faces 60a and 60b and rear flanges 61a and 61b, respectively. The applicator 50 is formed from a physiologically inert material, such as a relatively rigid plastic, and has all of its edges and ends smoothed and rounded to reduce the prospect of injuring the vagina during placement of the device 8.

FIGS. 8–10 illustrate how the applicator is used to place the barrier-type device 8. As shown in FIG. 8, the barrier-type device is carried on the applicator by the engagement of the forward end 56 in the groove 27 of the device 8 formed between the dome 10, the rim 12, and the posterior vaginal extension 14d. The brim 14 is grasped between the serrated surfaces 60a and 60b at the anterior vaginal extension 14c. The inserter 57 is retracted to the first position. In this position, the serrated faces 60a and 60b are forced together with the anterior vaginal extension 14c grasped between them. As the inserter 57 is drawn backward to the first position, the barrier-type device is stretched and retained on the applicator 50 by the tension of the flexible material from which the device 8 is formed. Thus arranged, the barrier-type device on the applicator 50 is placed intravaginally, with the device oriented as in FIG. 5.

After traversing the vaginal canal, the end 56 of the applicator 50 will place the posterior vaginal extension 14d of the brim against the posterior vaginal wall 42 and seat the rim 12 in the posterior fornix 39. When this occurs, the anterior vaginal extension 14c will still be forward of the anterior fornix 38. Next, the inserter 57 is slid forwardly in the main body 52 to the second position, which will move the anterior vaginal extension 14c against the anterior vaginal wall 40 and engage the rim 12 into the anterior fornix 38. When this occurs, the barrier-type device 8 will be retained in the engagement of FIG. 5 by the mechanisms described above.

Removal of the applicator can be understood with reference to FIGS. 9 and 10. When the barrier-type device is seated by forward movement of the inserter 57, the flexibility of the members 57a and 57b will cause the serrated faces 60a and 60b to spring apart slightly. Next, with the barrier-type device retained in position by suction, the upper member 57b is moved rearwardly toward the first position, which disengages the inserter from the anterior vaginal extension 14c of the brim. The lower member 57a is then pulled rearwardly. This completely disengages the applicator 52 from the anterior fornical extension 14c of the brim, and permits the applicator 52 to be removed.

Figure 11:
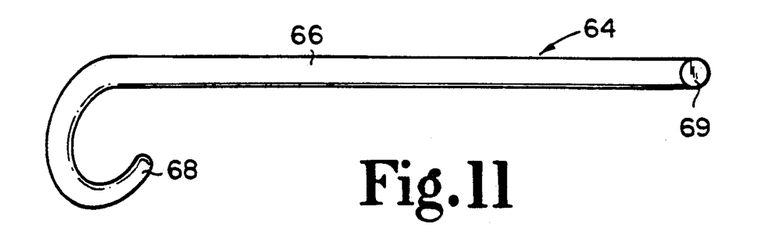
FIGS. 11 and 12 illustrate an extractor for removal of the barrier-type device from intravaginal placement.
Figure 12:
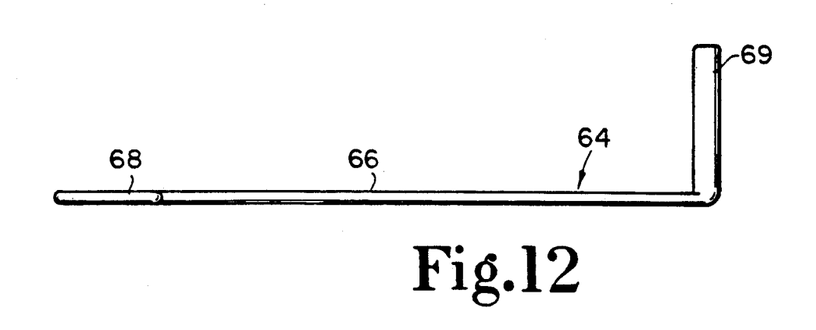
Figure 13:
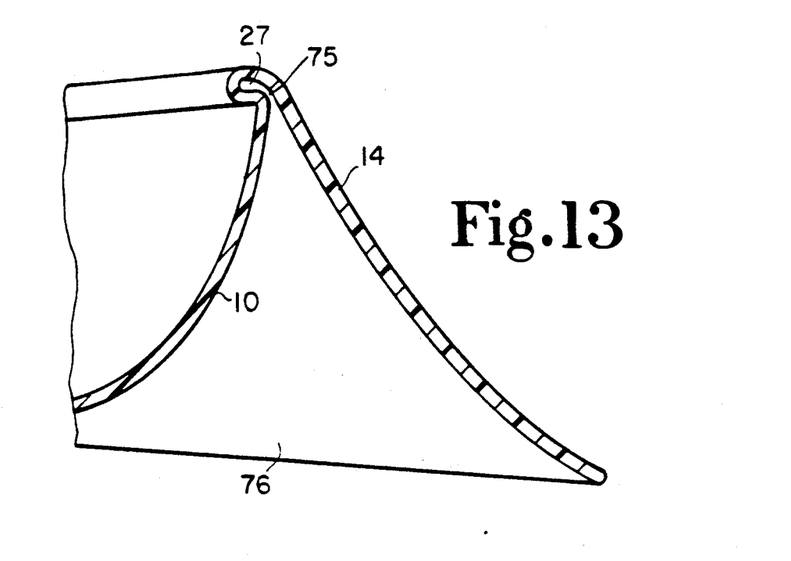
FIGS. 13 is an enlarged sectional view of a portion of the barrier-type device shown in FIG. 4.

As shown in FIGS. 11 and 12, an extractor 64 has an elongate portion 66 with a cross-section substantially flattened in a plane. The proximal tip of the elongate portion 66 transitions to a hook 68. The hook curves backwardly over the elongate portion and is flattened in the same plane. An operating handle 69 is attached to the distal end of the portion 66, to be substantially perpendicular to the plane of flattening of the portion and hooks.

The barrier-type device 8 is extracted by insertion of the elongate portion 66, hook first, flat into the vagina in the direction of the anterior fornix. When the anterior fornix is encountered, the extractor is rotated 90°, by the handle, to bring the hook 68 into engagement with the back of the brim 12 at the anterior vaginal location. The extractor is pulled out, bringing the device 8 with it.

Figures 14, 15:
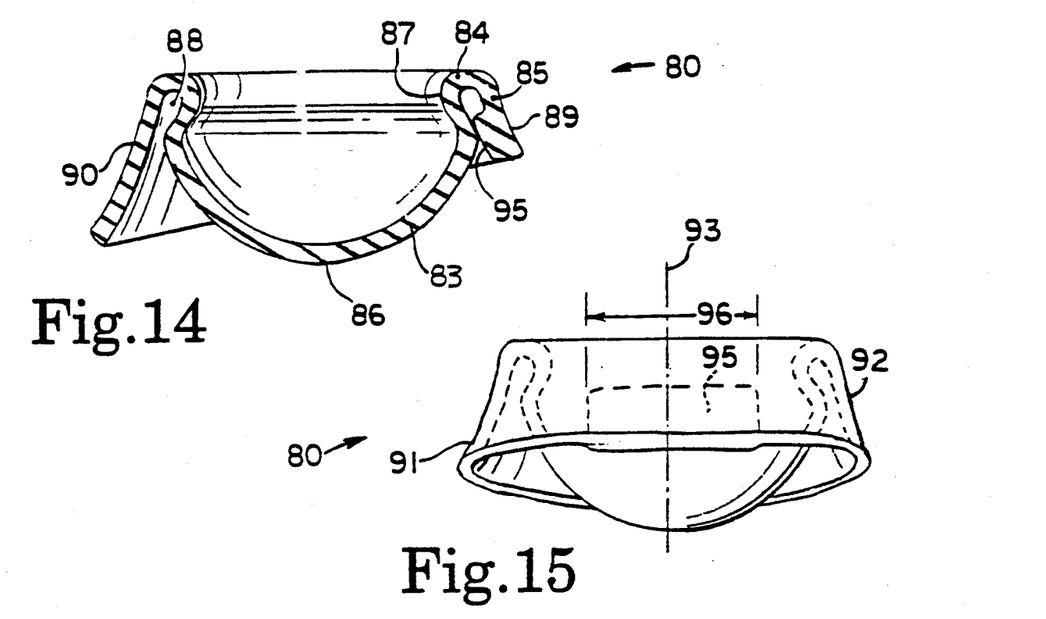
FIG. 14 is a cross-sectional side view of a barrier-type device in accordance with another embodiment of the present invention.
FIG. 15 is a rear elevational view of the device of FIG. 14.

Referring now to FIGS. 14–21, there is shown an intravaginal, barrier-type device 80 and a corresponding inserter 81 in accordance with another embodiment of the present invention. As with device 8 of FIGS. 1–4, device 80 also includes a cervical dome 83 and a fornical rim 84 which transitions by a backward fold to a vaginal brim 85. Dome 83 defines a peak or top 86, and the inward extension of rim 84 defines an annular lip 87. The backward fold of rim 84 at 87 forms an annular groove 88. Further, the circumferential symmetry and dimensions of brim 85 are as described for device 8 of FIG. 1-4. That is, the width of the brim increases continuously from the anterior to the posterior of device 80 such that the anterior extension 89 of brim 85 has a smaller vertical dimension than the posterior extension 90. The opposing lateral extensions 91 and 92 are symmetrical about centerplane 93 (FIG. 15). Anterior extension 89 defines a thickened grip portion 95 which extends inwardly from anterior extension 89 toward dome 83. Thickened grip portion 95 has a height roughly one-half the height of anterior extension 89 and a width 96 of approximately one inch.

Figures 19, 20, 21:
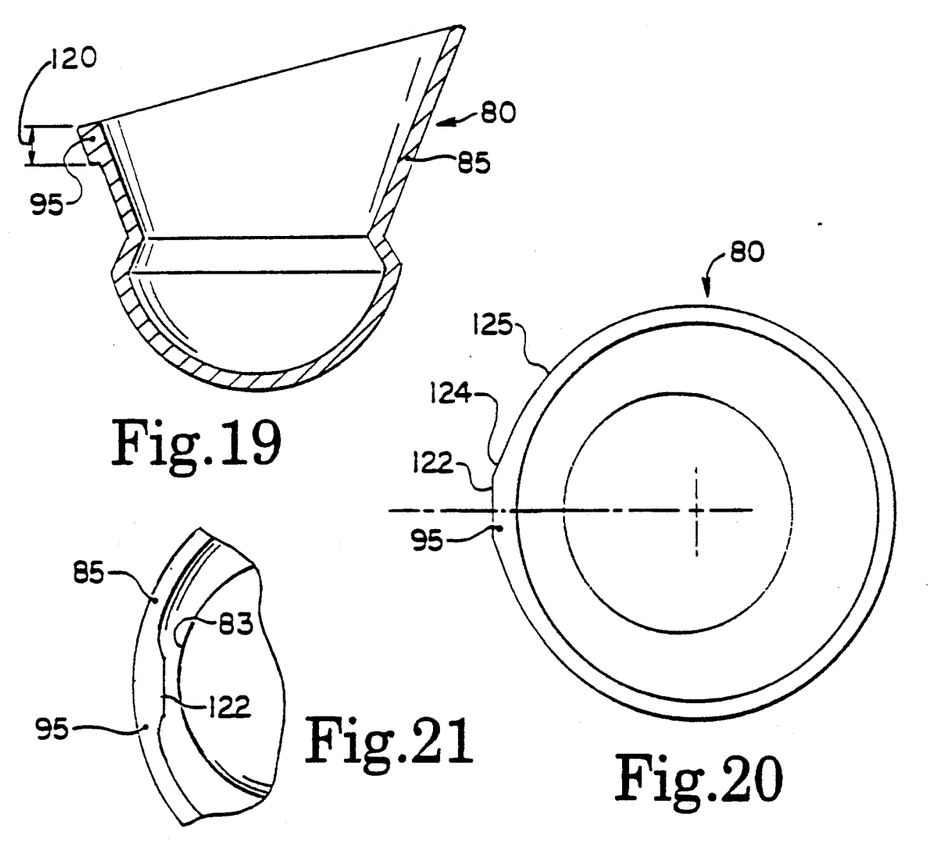
FIG. 19 is a cross-sectional side view of the barrier-type device of FIG. 14 shown with the vaginal brim unfolded.
FIG. 20 is a top view of the device of FIG. 19.
FIG. 21 is a bottom view of a portion of the device of FIG. 14 showing the contoured grasping surface formed by the thickened grip portion.

One method of manufacturing the device 80 of FIG. 14 is to mold the device unfolded as shown in FIG. 19. In one embodiment of this unfolded device 80, the thickened grip portion 95 has a height 120 which is roughly 0.2 inches (0.197 inches) and a width 96 (within which grip portion 95 has a thickness that is greater than that of brim 85 outside of width 95) of roughly 1.0 inch. When folded (FIG. 14), the vertical dimension or height of anterior extension 89 is 0.484 inches and the height of posterior extension 90 is 0.875 inches. In the unfolded condition (FIGS. 19 and 20), the central portion of grip portion 95 is flattened at 122 over a width of roughly 0.5 inches. Grip portion 95 then gently tapers therefrom (124) to the constant diameter remainder (125) of brim 85. When folded over (FIGS. 14 and 15), the flat portion 122 of grip portion 95, now faces dome 83 (FIG. 21).

Figures 16, 17:
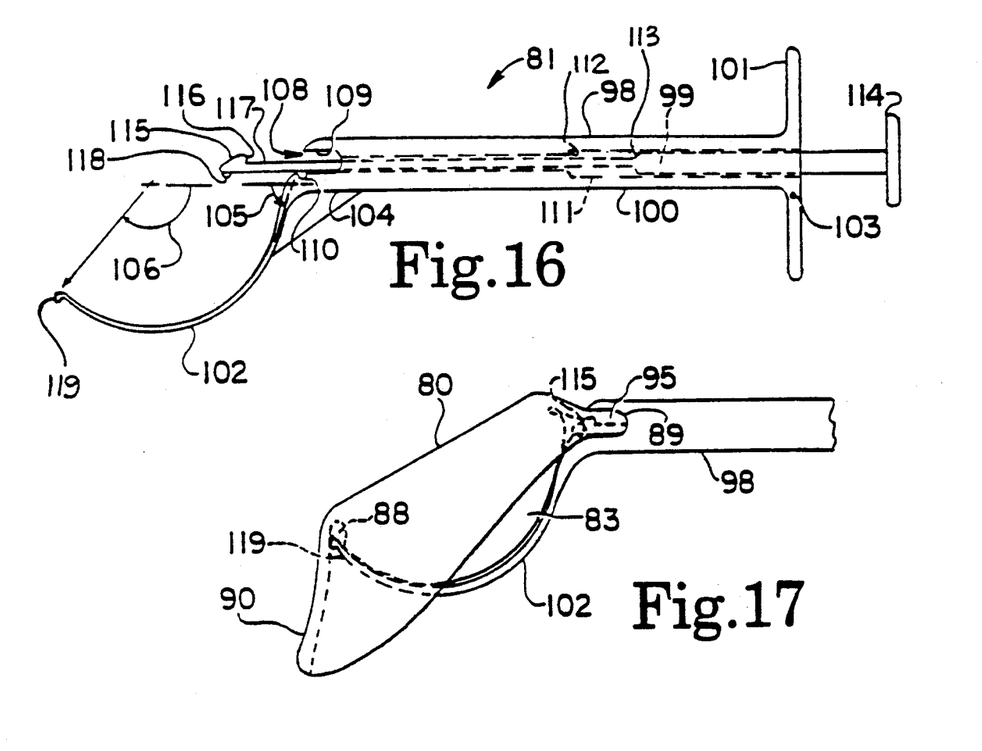
FIG. 16 is a side elevational view of the applicator in accordance with the preferred embodiment of the present invention.
FIG. 17 is a side view of the device of FIG. 14 shown gripped by the applicator of FIG. 16.

Referring now to FIG. 16, applicator 81 is made from a suitable plastic such as nylon and includes an elongate handle 98 and plunger 99. Handle 98 defines a central tubular body 100 which transitions at its distal end 103 into finger wall 101 and at its proximal end 104 into arcuate rigid support member 102. Support member 102 is a rigid arm, extends downwardly from proximal end 104 at an angle 105 of roughly 70°, and sweeps through an angle 106 of roughly 130°. Proximal end 104 defines an inwardly extending channel 108 having an upper wall 109. At the forward end of channel 108, proximal end 104 defines a notch 110. Handle 98 defines a generally rectangular passageway 111 extending all the way from distal end 103 to proximal end 104, with passageway 111 opening into channel 108. The passageway 111 further includes an intermediate shoulder 112 defining a transition between a distal portion of the passageway 111 of enlarged cross-sectional area and a proximal portion of the passageway 111 of reduced cross-sectional area.

Plunger 99 defines at its distal end an axially spaced finger disc 114. Proximally disposed from the finger disc 114 is an intermediate shoulder 113 defining a transition between a distal portion of the plunger 99 of enlarged cross-sectional area and a proximal portion of the plunger 99 of reduced cross-sectioned area. A proximal tip 115 of plunger 99 defines a ledge surface 116 oriented roughly orthogonally to the adjacent central body 117, thereby forming a hook for gripping barrier-type device 80 as described below. A nub 118 extends downwardly from proximal tip 115 and is adapted to engage with notch 110. Plunger 99 is positioned within handle 98 by inserting proximal tip 115 into passageway 111 at distal end 103 and telescopically sliding plunger 99 forwardly through passageway 111. The forward limit of movement of plunger 99 is defined by contact of its broad shoulder 113 against the complimentary shoulder 112 of the passageway 111. Applicator 81 may be grasped and manipulated by positioning two fingers on the forward side of finger wall 101 and positioning the thumb against the back side of finger disc 114 of plunger 99.

Figure 18:
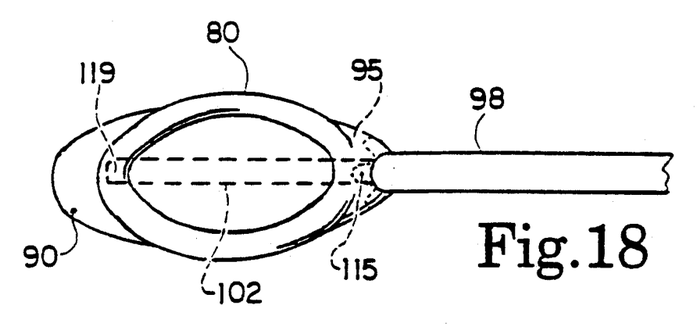
FIG. 18 is a top view of the device and applicator of FIG. 17.

In operation, a barrier-type device 80 is mounted to applicator 81 as shown in FIGS. 17 and 18. That is, posterior portion 90 is positioned over support member 102 such that the slightly outwardly curved proximal end 119 of support member 102 is lodged within groove 88, dome 83 is nested against and/or generally parallel to arcuate support member 102, and thickened portion 95 of anterior extension 89 is stretched over proximal tip 115 of plunger 99, with thickened grip portion 95 resting rearwardly of ledge surface 116. Plunger 99 is manually retracted from the release position shown in FIG. 16 to a gripping position shown in FIG. 17, whereby ledge surface 116 pulls thickened grip portion 95 into channel 108, gripping grip portion 95 between upper wall 109 and central body 117 and tip 115. Retraction of plunger 99 continues until nub 118 engages with notch 110, holding and locking device 80 firmly in position. Thus mounted on applicator 81, device 80 is positioned intravaginally as described above and shown generally in FIG. 5. After mounting the device 80 on applicator 81, the entire surface of device 80 is coated with contraceptive jelly. Proper positioning may be achieved by raising one leg onto a chair or toilet seat and spreading the labia while grasping distal end 103 and finger disc 114 and inserting the mounted device 80 with the applicator into the vagina with the open side and rim 84 pointing up, and positioning device 80 relative to the cervix as shown in FIGS. 5 and 6. To disengage applicator 81 from device 80 and remove applicator 81, plunger 99 is extended forwardly within passageway 111 by pushing finger disc 114 toward finger wall 101. This moves proximal tip 115 and central body 117 forwardly of proximal end 104 and pushes anterior extension 89 free from between upper wall 109 and central body 117. Applicator 81 is then disengaged from the device 80 by pulling the plunger 99 out all the way, followed by removal of remaining body 100. To remove device 80, the index and the middle finger are slid into the vagina. The index finger is placed between brim 85 and dome 83 into groove 88. A steady pressure is applied sideways to break the seal between the cap 80 and the cervix. Once the seal is broken, the middle finger is hooked over rim 84 and the whole cap 80 is pulled out of the vagina.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A kit for intravaginal, barrier-type prevention of conception and sexually-transmitted infection, comprising:
 a barrier-type device including:
  a cervical dome fabricated from a flexible material, said dome having an upwardly facing opening and a curved surface extending from said opening to a downwardly facing dome peak, and
  a continuous fornical rim on said dome, said rim defining said opening and transitioning therefrom into a continuous, annular vaginal brim which circumscribes said cervical dome and extends both outwardly and downwardly, and wherein said brim is made from said flexible material including an area of increased material wall thickness which defines a thickened grip portion extending inwardly toward said dome; and an inserter including:
    an elongated handle having at is proximal end arcuate support means for supporting said barrier-type device, and gripping means for releasably holding said device upon said support means during intravaginal positionment of said device; and
wherein said rim is folded from said dome inwardly, upwardly, and outwardly before transitioning into said brim, wherein said brim has an outer edge, and wherein the vertical dimension between said rim and the outer edge of said brim increases with circumferential symmetry from an anterior vaginal location on said brim to a posterior vaginal location on said brim which is opposite said anterior vaginal location.

2. The kit of claim 1, wherein said grip portion extends inwardly from said anterior vaginal location.

3. The kit of claim 2, wherein said grip portion has a height from the outer edge of roughly one half of the vertical dimension at the anterior vaginal location.

4. The kit of claim 2, wherein said grip portion has a height from the outer edge of approximately 0.2 inches.

5. The kit of claim 2, wherein said grip portion has a width of approximately 1.0 inch.

6. The kit of claim 2, wherein said gripping means includes a handle and plunger slidably disposed in said handle, the plunger having a proximal tip and the applicator being adapted to grip the brim at the anterior vaginal location between the proximal tip and the proximal end of the handle.

7. The kit of claim 6, wherein said support means includes a rigid support arm with a proximal end adapted to engage the device under the rim and between the dome and the brim at the posterior vaginal location when the brim at its anterior vaginal location is being gripped by the applicator.

8. The kit of claim 1, wherein said gripping means includes a plunger having a proximal tip, said plunger slidably disposed in said handle and being adapted to move between an extended release position whereby said tip is extended forwardly of said proximal end and a retracted gripping position whereby said tip is retracted to said proximal end to grip the device between the proximal end and the plunger.

9. The kit of claim 8, wherein the proximal end defines a forwardly opening channel and said plunger extends through a passageway in said handle and through and forwardly of the channel, said channel and plunger being adapted to receive the brim therebetween and within said channel in the gripping position.

10. The kit of claim 9, further including locking means for releasably locking said plunger in the gripping position.

11. The kit of claim 10, wherein said locking means includes a notch in the proximal end and a nub on said proximal tip, said nub adapted to engage with said notch and releasably hold said plunger stationary relative to said handle when said plunger has been retracted to said gripping position.

12. The kit of claim 10, wherein said proximal tip defines a hook adapted to engage and help grip the grip portion.

13. The kit of claim 12, wherein said arcuate support means has a proximal end, and wherein said inserter is adapted to hold the device by positioning the proximal end of said support means under the rim at the posterior vaginal location, between the brim and the dome, and by positioning the brim at the anterior vaginal location against said plunger just behind the hook and retracting said plunger to the gripping position whereby the brim at the anterior vaginal location is pulled into the channel.

14. The kit of claim 13, wherein said inserter is adapted to release from the device by extending the plunger to the release position.

15. A method of preventing conception and infection by sexually-transmitted diseases, comprising the steps of:
    providing a barrier-type device having:
        a cervical dome fabricated from a flexible material and having a fornical rim defining an upwardly facing opening, said rim being folded from said dome inwardly, upwardly, and outwardly, transitioning therefrom into a continuous, annular vaginal brim which circumscribes said dome and extends both outwardly and downwardly and wherein said brim is made from said flexible material including an area of increased material wall thickness which defines a thickened grip portion extending inwardly toward said dome; and
    placing the device in an intravaginal engagement which situates said dome in a cervical engagement with said rim fornically engaged and said vaginal brim in a continuous, sealing vaginal engagement; providing an applicator including:
        an elongated handle having at a proximal end thereof arcuate support means for supporting said barrier-type device, and
        gripping means for releasably holding said device upon said support means during intravaginal positionment of said device, and wherein said placing step includes using said applicator to place the device in the intravaginal engagement; and
    wherein said providing an applicator step includes said gripping means including a plunger slideably disposed in said handle, said plunger having a proximal tip extendable forwardly of the proximal end, and the applicator being adapted to grip the brim of the device between the proximal tip and the proximal end of the handle.

16. The method of claim 15, wherein said providing an applicator step includes the proximal tip defining a hook adapted to engage with and help grip the grip portion.

17. The method of claim 16, wherein said providing an applicator step includes said support means having a rigid support arm with a proximal end and wherein the proximal end of the handle defines a forwardly opening channel and said plunger extends through a passageway in said handle and through and forwardly of the channel, and wherein said placing step includes mounting the device to the applicator by positioning the proximal end of said support arm under the rim, between the brim and the dome at the posterior vaginal location, and positioning the brim at the anterior vaginal location against said plunger just behind the hook and retracting said plunger to a gripping position whereby the thickened portion of the brim is pulled into and held in the channel.

18. The method of claim 17, further including releasing the device from the applicator by extending the plunger to a release position whereby the proximal tip is extended forwardly and away from the proximal end of the handle.

19. The method of claim 17, wherein said providing an applicator step includes said applicator including locking means for releasably locking said plunger in the gripping position.

20. The method of claim 19, wherein said providing an applicator step includes said locking means including a notch in the proximal end of said handle and a nub on said proximal tip, said nub adapted to engage with said notch and releasably hold said plunger stationary relative to said handle when said plunger has been retracted to said gripping position.

21. An applicator for intravaginally positioning a barrier-type device for preventing conception and infection by sexually-transmitted diseases, comprising:

an elongate handle having at a proximal end thereof arcuate support means including a concavity for supporting a barrier-type device having a dome portion sized to be received in said concavity; and gripping means operative at the proximal end of said handle and having a proximal tip, for releasably holding the device upon said support means during intravaginal positionment of the device.

22. The applicator of claim 21, wherein the device has a dome which transitions to a continuous fornical rim which transitions to an outwardly and downwardly extending brim and wherein said gripping means includes a plunger slidably disposed in said handle, the applicator adapted to grip the brim of a device between the proximal tip and the proximal end of the handle.

23. The applicator of claim 22, wherein said support means includes a rigid support arm with a proximal end adapted to engage the device between the dome and the brim at a point opposite where the brim is gripped by the proximal tip and the proximal end of the handle.

24. The applicator of claim 21, wherein said gripping means includes a plunger having a proximal tip, being slidably disposed in said handle, and being adapted to move between an extended release position whereby said proximal tip is extended forwardly of said proximal end of said handle and a retracted gripping position whereby said proximal tip is retracted to said proximal end to grip the device between the proximal end and the plunger.

25. The applicator of claim 24 wherein the device includes a brim and wherein the proximal end defines a forwardly opening channel and said plunger extends through a passageway in said handle and through and forwardly of the channel, said channel and plunger being adapted to receive the brim therebetween and within said channel in the gripping position.

26. The applicator of claim 25, further including locking means for releasably locking said plunger in the gripping position.

27. The applicator of claim 26, wherein said locking means includes a notch in the proximal end of the handle and a nub on said proximal tip, said nub adapted to engage with said notch and releasably hold said plunger stationary relative to said handle when said plunger has been retracted to said gripping position.

28. The applicator of claim 27, wherein the brim of the device defines a thickened grip portion and wherein said proximal tip defines a hook adapted to engage and grip the grip portion.

29. The applicator of claim 28, wherein the device includes a cervical dome having a downwardly facing dome peak and a curved surface leading from the peak to a continuous fornical rim defining an upwardly facing opening, the rim transitioning from the opening to the brim which is a continuous, annular vaginal brim which circumscribes the cervical dome and extends both outwardly and downwardly, and wherein said arcuate support means has a proximal end, and wherein the applicator is adapted to hold the device by positioning the proximal end of said support means under the rim, between the brim and the dome, and by positioning an opposite portion of the brim against said plunger just behind the hook and retracting said plunger to the gripping position whereby the opposite portion of the brim is pulled into the channel.

30. The applicator of claim 29, wherein the brim of the device defines a thickened grip portion and wherein said applicator is adapted to receive and grip said grip portion within the channel.

* * * * *